(12) United States Patent
Park et al.

(10) Patent No.: US 8,741,594 B2
(45) Date of Patent: Jun. 3, 2014

(54) MITOCHONDRIAL ENOYL COENZYME A HYDRATASE 1 AS MARKER FOR DIAGNOSING STOMACH CANCER

(75) Inventors: Won Sun Park, Busan (KR); Jae-Hong Ko, Cheju (KR); Na Ri Kim, Busan (KR); Jin Han, Busan (KR); Hyoung Kyu Kim, Gyeonggi-do (KR); Mohamad Warda, Busan (KR)

(73) Assignee: Inje University Industry-Academic Cooperation Foundation, Gimhae (KR)

( * ) Notice: Subject to any disclaimer, the term of this patent is extended or adjusted under 35 U.S.C. 154(b) by 1349 days.

(21) Appl. No.: 12/009,350

(22) Filed: Jan. 17, 2008

(65) Prior Publication Data
US 2008/0213816 A1 Sep. 4, 2008

(30) Foreign Application Priority Data
Jan. 17, 2007 (KR) .................. 10-2007-0005212

(51) Int. Cl.
*C12Q 1/26* (2006.01)

(52) U.S. Cl.
USPC ........................................ 435/25; 530/387.7

(58) Field of Classification Search
USPC ........................................ 435/25; 530/387.7
See application file for complete search history.

(56) References Cited

U.S. PATENT DOCUMENTS

2007/0172900 A1 * 7/2007 Cahill et al. ................. 435/7.23

FOREIGN PATENT DOCUMENTS

WO  WO 2005/078124 A2 * 8/2005 .............. C12Q 1/68

OTHER PUBLICATIONS

Kim et al., "Mitochondrial alterations in human gastric carcinoma cell line", AJP-Cell Physiology,Epub May 30, 2007, pp. C761-C771.*
Ryu et al., "The Proteomics Approach to Find Biomarkers in gastric Cancer", Journal of Korean med Sci, 2003, vol. 18, p. 505-509.*
Srinivas et al. "Trends in biomarker research for cancer detection." (2001) The Lancet: Oncology, vol. 2: 698-704.*

* cited by examiner

*Primary Examiner* — Jon P Weber
*Assistant Examiner* — Teresa E Knight
(74) *Attorney, Agent, or Firm* — Steptoe & Johnson LLP

(57) ABSTRACT

The present invention relates to mitochondrial protein that can be used as a marker for diagnosing stomach cancer. According to the present invention, the marker for diagnosing stomach cancer comprises mitochondrial enoyl coenzyme A hydratase 1.

2 Claims, 4 Drawing Sheets
(3 of 4 Drawing Sheet(s) Filed in Color)

FIG. 3

| SPOT NO. | GENE BANK ID | PROTEIN IDENTIFICATION | CHANGE IN AGS (%) | KNOWN FUNCTION |
|---|---|---|---|---|
| 35 | 14286220 | MITOCHONDRIAL SHORT-CHAIN ENOYL COENZYME A HYDRATASE 1 | 996 | FATTY ACID METABOLISM-RELATED ENZYME |

SEQUENCE LISTING

<160> NUMBER OF SEQ ID NOS: 1

<210> SEQ ID NO 1
<211> LENGTH: 290
<212> TYPE: PRT
<213> ORGANISM: human

<400> SEQUENCE: 1

```
Met Ala Ala Leu Arg Val Leu Leu Ser Cys Val Arg Gly Pro Leu Arg
1               5                   10                  15

Pro Pro Val Arg Cys Pro Ala Trp Arg Pro Phe Ala Ser Gly Ala Asn
            20                  25                  30

Phe Glu Tyr Ile Ile Ala Glu Lys Arg Gly Lys Asn Asn Thr Val Gly
        35                  40                  45

Leu Ile Gln Leu Asn Arg Pro Lys Ala Leu Asn Ala Leu Cys Asp Gly
    50                  55                  60

Leu Ile Asp Glu Leu Asn Gln Ala Leu Lys Ile Phe Glu Glu Asp Pro
65                  70                  75                  80

Ala Val Gly Ala Ile Val Leu Thr Gly Gly Asp Lys Ala Phe Ala Ala
                85                  90                  95

Gly Ala Asp Ile Lys Glu Met Gln Asn Leu Ser Phe Gln Asp Cys Tyr
            100                 105                 110

Ser Ser Lys Phe Leu Lys His Trp Asp His Leu Thr Gln Val Lys Lys
        115                 120                 125

Pro Val Ile Ala Ala Val Asn Gly Tyr Ala Phe Gly Gly Gly Cys Glu
    130                 135                 140

Leu Ala Met Met Cys Asp Ile Ile Tyr Ala Gly Glu Lys Ala Gln Phe
145                 150                 155                 160

Ala Gln Pro Glu Ile Leu Ile Gly Thr Ile Pro Gly Ala Gly Gly Thr
                165                 170                 175
```

-continued

```
Gln Arg Leu Thr Arg Ala Val Gly Lys Ser Leu Ala Met Glu Met Val
            180                 185                 190

Leu Thr Gly Asp Arg Ile Ser Ala Gln Asp Ala Lys Gln Ala Gly Leu
            195                 200                 205

Val Ser Lys Ile Cys Pro Val Glu Thr Leu Val Glu Glu Ala Ile Gln
    210                 215                 220

Cys Ala Glu Lys Ile Ala Ser Asn Ser Lys Ile Val Ala Met Ala
225                 230                 235                 240

Lys Glu Ser Val Asn Ala Ala Phe Glu Met Thr Leu Thr Glu Gly Ser
                245                 250                 255

Lys Leu Glu Lys Lys Leu Phe Tyr Ser Thr Phe Ala Thr Asp Asp Arg
            260                 265                 270

Lys Glu Gly Met Thr Ala Phe Val Glu Lys Arg Lys Ala Asn Phe Lys
            275                 280                 285

Asp Gln
    290
```

MITOCHONDRIAL ENOYL COENZYME A HYDRATASE 1 AS MARKER FOR DIAGNOSING STOMACH CANCER

CROSS-REFERENCE TO RELATED APPLICATION

This application claims priority to and the benefit of Korean Patent Application No. 10-2007-0005212 filed in the Korean Intellectual Property Office on Jan. 17, 2007, the entire content of which is incorporated herein by reference.

FIELD OF THE INVENTION

The present invention relates to mitochondrial protein that can be used as a marker for diagnosing stomach cancer, and more particularly, to protein showing a higher expression level in a stomach cancer cell than in a normal cell, and a composition and a method for diagnosing stomach cancer by using the protein, and a method for screening a drug for treating, suppressing or preventing stomach cancer.

BACKGROUND OF THE INVENTION

Stomach cancer is the most common cancer in Asia (especially, in Korea and Japan), which shows the highest mortality rate. Accordingly, it is very necessary to diagnose stomach cancer as early as possible.

To this end, many approaches to find various biological marker materials from cells or bloods have been made. However, it has been difficult to find an effective marker material due to lack of technological information and measuring equipments.

Despite the above difficulties, it has been known that the structural or functional change of mitochondria is closely related to generation of cancer as a result of a research to prove a relationship between mitochondria and cancer. However, such a research has not provided sufficient information on mitochondria of protein that most actively functions in a body.

Surprisingly, the present inventors discovered that mitochondrial enoyl coenzyme A hydratase 1 can be used as a novel material to diagnose cancer and develop a material for anticancer therapy.

SUMMARY OF THE INVENTION

It is, therefore, one object of the present invention to provide mitochondrial enoyl coenzyme A hydratase 1 as a marker for diagnosing stomach cancer.

It is another object of the present invention to provide a composition for diagnosing stomach cancer by using the mitochondrial enoyl coenzyme A hydratase 1, a method of diagnosing stomach cancer, and a method of screening a drug for treating, suppressing or preventing stomach cancer.

The configurations of the present invention for accomplishing the above objects are as follows.

A physiological marker material for diagnosing stomach cancer has been actively developed. During the above development, the present inventors noted that mitochondria, which are a cellular organelle and abundant in a cell, are related to generation of cancer, and thus, compared the mitochondrial protein of a human stomach cancer cell line with that of a normal stomach cell line to develop mitochondrial protein as a marker material for stomach cancer.

For the purpose of comparison, two-dimensional electrophoresis analysis has been performed. The two-dimensional electrophoresis is a method for recognizing a physical change of protein in a cell or a tissue with an electric field being applied thereto, and comparing one kind of protein with another based on the change. Such two-dimensional electrophoresis is comprised of one-dimensional isoelectric point isolation and two-dimensional protein mass gel isolation.

Seeing the images of the protein widely spread on a gel through the two-step protein isolation, two kinds of protein that have significant differences in their quantitative expressions can be obtained. Then, the mass of the peptide of the obtained protein can be measured through a molecular mass spectrometry called MALDI-TOF MS. Based on the measured mass of the peptide, the mass of the amino acid constituting the peptide can be calculated, and with reference to a database of the masses of peptides, the obtained protein can be known based on the calculated mass of the amino acid.

By following the above steps, the present inventors discovered mitochondrial enoyl coenzyme A hydratase 1, which was nine times more specifically expressed in the mitochondria of a stomach cancer cell. Further, the present inventors believe that diagnosing whether a subject suspected of stomach cancer is attacked would become easier.

In one aspect of the present invention, there is provided a marker for diagnosing stomach cancer, which comprises mitochondrial enoyl coenzyme A hydratase 1. Herein, the mitochondrial enoyl coenzyme A hydratase 1 is known as an enzyme involved in fatty acid metabolism, and is provided with NCBI Gene Bank Accession No. 14286220.

In another aspect of the present invention, there is provided a composition for diagnosing stomach cancer, which comprises an antibody specific to mitochondrial enoyl coenzyme A hydratase 1 or an immunogenic fragment thereof. Herein, the immunogenic fragment refers to a part or a portion of full-length protein that brings about in vivo immunoreactions and can be recognized by an antibody specific to protein in accordance with the present invention.

Preferably, the antibody in accordance with the present invention may be a polyclonal or monoclonal one, or a fragment thereof, if it has an antigen-binding property. Further, all kinds of immunoglobulin antibodies may be the antibody in accordance with the present invention. Furthermore, a monoclonal antibody is particularly preferable. The antibody in accordance with the present invention can be prepared by injecting and subsequently purifying marker protein or a fragment thereof in accordance with the present invention into a host (for example, a mammal such as a mouse and a rat), following a conventional method known to those skilled in the art, or can be purchased from a proper source. Specifically, the monoclonal antibody can be prepared based on the conventional technology for generating an immortalized cell line or the conventional phage antibody library, or can be purchased from a proper source (e.g., an ECHS1 antibody or a clone 1G9 from Novus). The antibody can be typically administered together with an adjuvant to increase its antigenicity.

The composition for diagnosis in accordance with the present invention can be prepared by using the mitochondrial enoyl coenzyme A hydratase 1, which is the marker for diagnosing stomach cancer, and may further comprise a tool or a reagent used for immunological analysis.

In yet another aspect of the present invention, there is provided a method of diagnosing stomach cancer, which comprises the steps of picking a cell from a subject, and measuring the expression amount of mitochondrial enoyl coenzyme A hydratase 1 in the cell. Herein, the subject may be a mammal, and particularly, a human being.

In still yet another aspect of the present invention, there is provided a method of screening a drug for treating, suppressing or preventing stomach cancer, which comprises the steps of contacting with a test material a cell obtained from a stomach cancer cell line, and measuring the change in the expression amount of mitochondrial enoyl coenzyme A hydratase 1 in the cell.

Herein, the change in the expression amount of the mitochondrial enoyl coenzyme A hydratase 1 can be measured in the same way that the change in other protein, which is used as a marker for diagnosing stomach cancer, is measured in a biological sample following the conventional technology. For example, two-dimensional electrophoresis, Western blot, ELISA (Enzyme-Linked ImmunoSorbent Assay), radioimmunoassay, radioimmunodiffusion, immunohistochemistry assay, immunoprecipitation assay, FACS, and protein chip, etc. can be employed, but a person skilled in the art needs not be restricted from employing others. Further, the expression amount of the marker can be indirectly measured by measuring its mRNA level. Assays for doing so include, but are not limited to, RT-PCR, DNA chip assay, etc.

BRIEF DESCRIPTION OF THE DRAWINGS

The patent or application file contains at least one drawing executed in color. Copies of this patent or patent application publication with color drawing(s) will be provided by the Office upon request and payment of the necessary fee The above objects and features of the present invention will become more apparent from the following description of the preferred embodiments given in conjunction with the accompanying drawings, in which:

FIG. 1, including

FIG. 3 shows an analysis result of the No. 35 protein obtained through the MALDI-TOF MS analysis. Seeing the result, it is found that the No. 35 protein is mitochondrial enoyl coenzyme A hydratase 1.

DETAILED DESCRIPTIONS OF THE PREFERRED EMBODIMENTS

Figure 1A:
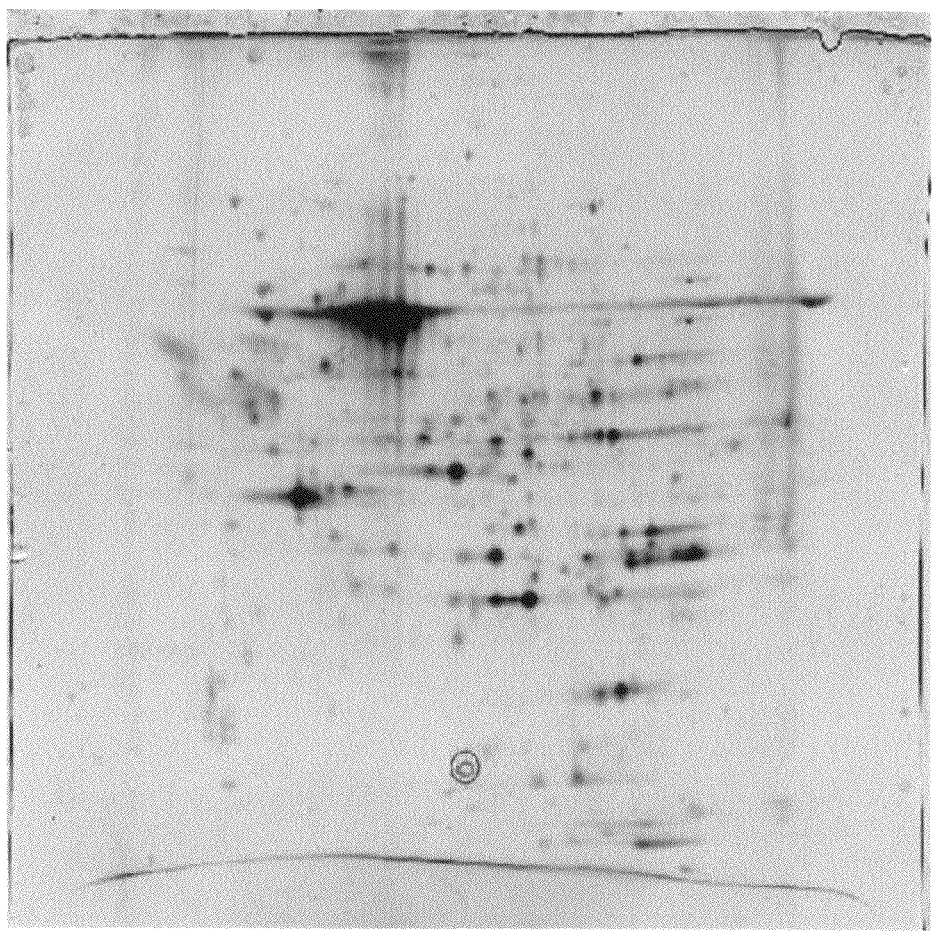
FIG. 1A and FIG. 1B, is a photograph of a gel obtained by two-dimensional electrophoresis performed to observe the change in mitochondrial protein of a stomach cancer cell. The gel photograph shown in FIG. 1A is the analysis result for the mitochondrial protein of a normal stomach cell. The gel photograph shown in FIG. 1B is the analysis result for the mitochondrial protein of a stomach cancer cell. The spots marked as circles in FIGS. 1A and 1B are No. 35 protein described below.
Figure 1B:
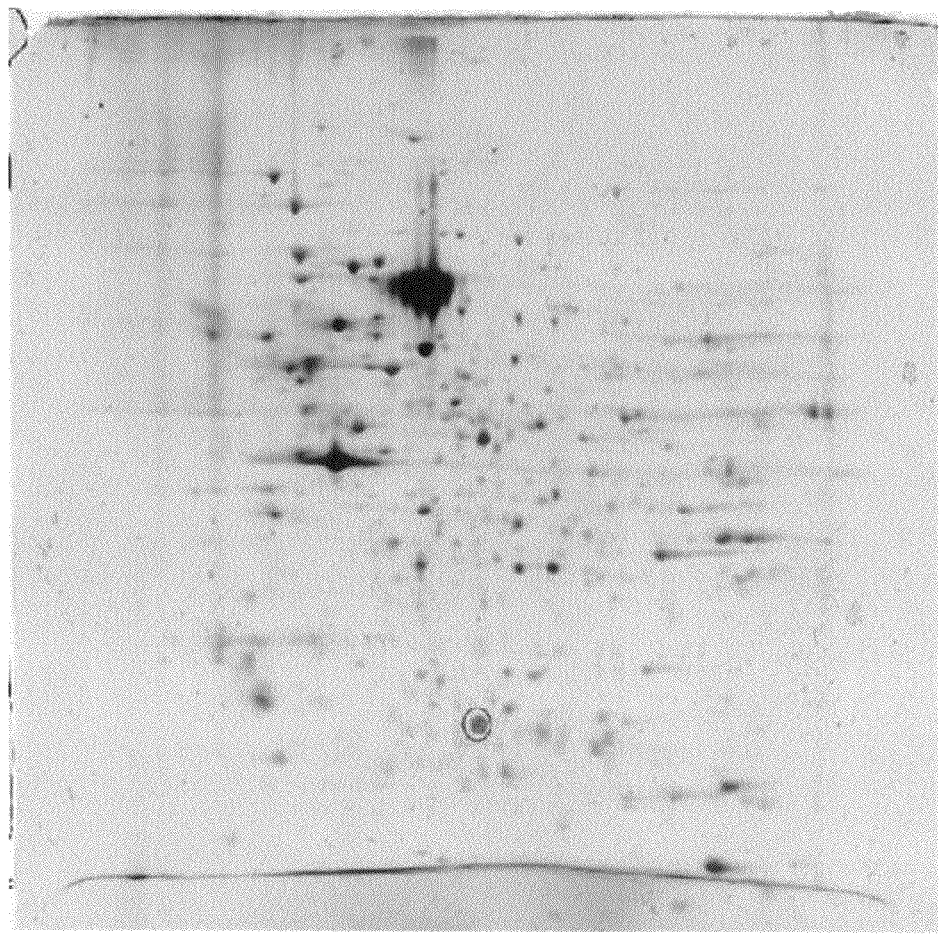
Figure 2:
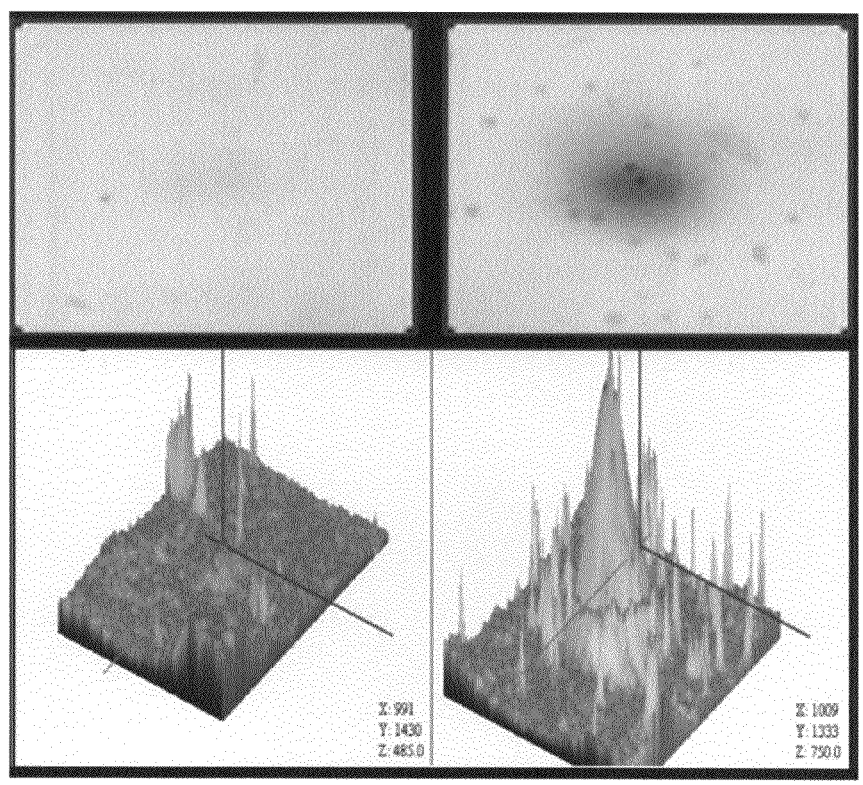
FIG. 2 shows a protein image indicative of a significant difference between a normal cell and a stomach cancer cell. The protein image is obtained by the two-dimensional electrophoresis of FIGS. 1a and 1b. The upper part of FIG. 2 is a magnified protein image showing a significant difference between the normal cell and the stomach cancer cell, and the lower part of FIG. 2 is a three-dimensional cubic image thereof, wherein the left image is of the normal cell, and the right image is of the stomach cancer cell. The over-expressed protein in the stomach cancer cell is No. 35 protein.

Hereinafter, the present invention will be described in more detail with reference to non-limiting examples.

EXAMPLES

Cell Cultivation

A normal stomach cell line (RGM-1) and a stomach cancer cell line (AGS) were prepared for two-dimensional electrophoresis analysis. 50 ml of FBS and 5 ml of penicillin/streptomycin were mixed into either of 455 ml of DMEM F/12 and 455 ml of RPMI 1640, to prepare a medium. 10 ml of the prepared medium was put into a tube having a capacity of 15 ml, and then mixed with a prepared cell. The supernatant was removed by centrifugation (12,000 rpm, five minutes), 5 ml of the medium was added again, and the mixture was vortexed, and thereby, a cell suspension was obtained. 10 ml of the medium were plated over a culture plate in advance, and then 5 ml of the cell suspension were put into the culture plate so that the suspension could be evenly spread out throughout the plate. After ensuring that cells were evenly spread out with a microscope, the plate was cultivated in a $CO_2$ incubator (37° C., 50 ml/L of $CO_2$-containing humidifying atmosphere).

Preparation of a Mitochondrial Sample for Two-Dimensional Electrophoresis

AGS and RGM cell lines, which were isolated from the plate by trypsin digestion, were mixed with a mitochondria-isolated solution of pH 7.4 containing 50 mM sucrose, 200 mM mannitol, 5 mM potassium phosphate, 1 mM EGTA, 5 mM MOPS, 0.1% BSA and a protease inhibitor cocktail in a medium fitting glass-teflon potter-Elvehjem homogenizer. The mixture was six to seven times crushed and thereby homogenized in a glass tube to disrupt cell membranes. The homogenized cells were shifted to a centrifuge tube and centrifuged under the pressure of 1,500-fold gravity at 4° C. for five minutes to remove cell appendages having a large density. The supernatant was shifted to a new centrifuge tube and centrifuged under the pressure of 10,000-fold gravity at 4 □ for ten minutes. The precipitates were in a pellet form containing highly concentrated mitochondria. The supernatant was removed, and the pellet was put into a protein lysate solution containing 7M urea, 2M thiourea, 4% CHAPS, 40 mM Tris base, 1% DTT, 0.5% IPG buffer, 0.5% Triton X-114 and protease inhibitor, and thereby, dissolved at a room temperature for about one hour. The mitochondrial protein dissolved in the lysate solution was quantitatively titrated with a 2D Quant kit (GE Healthcare, U.S.A.), and the resultant product was used in the two-dimensional electrophoresis protein isolation phase.

Two-Dimensional Electrophoresis Protein Isolation

First Protein Isoelectric Point Isolation

By utilizing an isoelectric point, which is an intrinsic property of protein, protein can be isolated first. 250 µl of an isoelectric point isolation solution containing 50 µg of protein was added to 13 cm of a dried IPG (Immobilized PH Gradient) strip, and a rehydration process continued for more than ten hours. The isoelectric point isolation was performed on a re-hydrated IPG strip with an IPG phore device (GE Healthcare, U.S.A.). The isoelectric point isolation was performed under 500 volts for one hour, 1,000 volts for one hour, and finally 8,000 volts until the accumulated voltage reaches up to 60,000 volts. In this case, the highest current was controlled within 50 µA per strip. The strip after the isoelectric point isolation was slowly stirred in a first hybridizing solution (a 50 mM Tris-HCl solution of pH 8.8 containing 6M urea, 30% glycerol, 2% SDS, bromophenol blue and 1% DTT) for fifteen minutes. The strip after the first hybridization was dipped into a second hybridizing solution (a 50 mM Tris-HCl solution of pH 8.8 containing 6M urea, 30% glycerol, 2% SDS, bromophenol blue and 2.5% iodoacetamide) and stirred again for fifteen minutes.

Two-Dimensional Protein Electrophoresis

Protein can then be isolated, depending on its molecular weight in a polyacrylamide gel. 12.5% of a sodium dodecyl sulfate polyacrylamide gel was made, fitting to the 13 cm size through an SE 600 Ruby electrophoresis set (Amersham, U.S.A.). The strip after the hybridization process was put on a gel, and the gap between the strip and the gel was sealed with a sealing agar. A running buffer (25 mM Tris, 192 mM glycine, 2.5 mM SDS, pH 8.3) was filled in the set, the protein of the strip was shifted to the gel at eighty volts for the first twenty minutes, and then electrophoresis was performed at 240 volts for about five hours. The gel after the electrophoresis was stained by silver nitrate.

Scanning Gel and Analyzing Image

The stained gel was scanned through a flat scanner (UMAX Power Look 1100, U.S.A.). When scanning, the functional options were 300 dpi and a transmission type. The image of the scanned gel was analyzed through an image analysis program (Image Master 2D Platinum, GE Healthcare, U.S.A.). In the present invention, final protein identification was performed after selecting protein showing more than 170% differences in two cell lines by the image analysis.

Protein Identification

After collecting protein (i.e., No. 35 protein) showing a remarkable difference in two used cell lines, the protein mass spectrometry employing the MALDI-TOF MS technique was performed by IN2GEN (Korea). When searching for an analyzed protein mass peak based on the NCBI database in MASCOT PMF, it was found that the peak indicates the mitochondrial enoyl coenzyme A hydratase 1 (Gene Bank ID 14286220). The identified sequences of the protein (SEQ ID NO: 1) were as follows:

maalrvllsc vrgplrppvr cpawrpfasg anfeyiiaek rgknntvgli qlnrpkalna
61 lcdglideln qalkifeedp avgaivltgg dkafaagadi kemqnlsfqd cysskflkhw
121 dhltqvkkpv iaavngyafg ggcelammcd iiyagekaqf aqpeiligti pgaggtqrlt
181 ravgkslame mvltgdrisa qdakqaglvs kicpvetlve eaiqcaekia snskivvama
241 kesvnaafem tltegsklek klfystfatd drkegmtafv ekrkanfkdq This protein was nine times more specifically expressed in a stomach cancer cell line than in a normal cell line.

EFFECTS OF THE INVENTION

Therefore, according to the present invention, a material called mitochondrial enoyl coenzyme A hydratase 1, which is nine times more specifically expressed in the mitochondria of a stomach cancer cell line than in a normal cell line, was discovered by the two-dimensional electrophoresis analysis described above. Accordingly, it would be possible to early diagnose stomach cancer of a subject with the material.

While the invention has been shown and described with respect to the preferred embodiments, it will be understood by those skilled in the art that various changes and modifications may be made without departing from the spirit and the scope of the invention as defined in the following claims.

What is claimed is:

1. A method of diagnosing stomach cancer in a mammal, comprising the steps of:
   isolating a cell from the stomach of a mammal suspected of or at risk for having stomach cancer;
   measuring the amount of mitochondrial enoyl coenzyme A hydratase 1 from the cell;
   comparing the measured amount of the mitochondrial enoyl coenzyme A hydratase 1 from the isolated stomach cell to a measured amount of mitochondrial enoyl coenzyme A hydratase 1 from a normal cell,
   wherein the cell isolated from the stomach is a stomach cancer cell when the amount of mitochondrial enoyl coenzyme A hydratase 1 in the isolated cell is at least about nine times more than the amount of mitochondrial enoyl coenzyme A hydratase 1 in the normal cell.

2. The method according to claim 1, wherein the amount of mitochondrial enoyl coenzyme A hydratase 1 in the cell isolated from the stomach is measured by a two-dimensional electrophoresis analysis.

* * * * *